United States Patent [19]

Vahaviolos

[11] 4,017,810
[45] Apr. 12, 1977

[54] VOLTAGE CONTROLLED OSCILLATOR

[75] Inventor: Sotirios John Vahaviolos, East Windsor Township, Mercer County, N.J.

[73] Assignee: Western Electric Company, Inc., New York, N.Y.

[22] Filed: Apr. 1, 1976

[21] Appl. No.: 672,825

Related U.S. Application Data

[62] Division of Ser. No. 592,437, July 2, 1975, Pat. No. 3,965,726.

[52] U.S. Cl. .................................. 332/14; 324/120; 331/49; 331/177 R; 332/21; 332/22; 332/23 R
[51] Int. Cl.² ..................... G01R 19/26; H03K 7/06
[58] Field of Search ............ 331/46, 49, 56, 177 R, 331/177 V; 332/9 R, 14, 21, 22, 23 R; 324/120

[56] References Cited

OTHER PUBLICATIONS

Peterson, "Isolated Multiple Oscillators Provide Wide Frequency Range" Electronics, Apr. 17, 1967, pp. 90, 91.

Primary Examiner—Siegfried H. Grimm
Attorney, Agent, or Firm—E. W. Pfeifle; D. J. Kirk

[57] ABSTRACT

A plurality of window comparators and voltage controlled oscillators are arranged to receive analog input signals which are converted to output frequencies that are linearly proportional to the analog signals over a substantially infinite amplitude range.

4 Claims, 6 Drawing Figures

VOLTAGE CONTROLLED OSCILLATOR

CROSS REFERENCE TO RELATED APPLICATION

This is a division of application Ser. No. 592,437, filed July 2, 1975 and issued as U.S. Pat. No. 3,965,726 on June 29, 1976 which is related to "Method and Apparatus for the Real-Time Evaluation of Welds by Emitted Stress Waves." Said patent is assigned to the same assignee as the instant invention.

BACKGROUND OF THE INVENTION

1. Field of the Invention

This invention relates to a signal processing apparatus. In particular, the invention is directed to such a signal processing apparatus having a continuously variable linear voltage controlled oscillator therein.

2. Description of the Prior Art

Voltage controlled oscillators are well known in the prior art. Such an oscillator will accept an analog voltage input signal over some full-scale operating range and generate an output frequency which is linearly proportional to the amplitude of the analog voltage signal. Such oscillators have found many applications where the ratio of the maximum to the minimum analog voltage input signal amplitude is about 10:1.

However, once this ratio is exceeded, the output frequency is no longer linearly proportional to the analog input signal and becomes distorted and unreliable. Compensation for such non-linearity may be made using non-linear amplification circuitry. However, such circuitry is relatively sophisticated, bulky and expensive.

BRIEF SUMMARY OF THE INVENTION

The foregoing problem has been overcome with the instant voltage-controlled oscillator circuit which receives an analog input signal and generates an output frequency which is linearly proportional to the analog input signal over a substantially infinite range. The circuit is comprised of a plurality of window comparators which simultaneously receive the analog input signal, each comparator being responsive to a predetermined different range of the maximum analog input signal amplitude to generate an enable signal. A plurality of voltage-controlled oscillators also simultaneously receive the same analog input signal and each is responsive to the enable signal from a different one of the window comparators to generate a frequency modulated output signal which is linearly proportional to the analog input signal within the predetermined range.

Advantageously, the instant voltage controlled oscillator provides relatively inexpensive circuitry which is linear over a substantially infinite range of analog input signals.

BRIEF DESCRIPTION OF THE DRAWINGS

Referring now to the drawings, in which like numerals represent like parts in the several views.

DESCRIPTION OF THE PREFERRED EMBODIMENTS

The present invention, relating to an improved voltage controlled oscillator arrangement is described in relation to a method and apparatus for the real-time evaluation of welds by using emitted stress waves. However, it will be understood that such description is exemplary and is for purposes of exposition and not for purposes of limitation. It will be readily appreciated that the instant voltage-controlled oscillator can be advantageously used in any circuit arrangement wherein an analog input signal is to be converted to an output frequency that is linearly proportional to the analog input signal.

The welding process occurs by mechanically holding articles to be welded together, melting the parts at their common interface, causing molten material to flow from both articles, and resolidifying the molten volume. The volume where melting occurs is generally called the molten-resolidification zone or weld nugget, while the region where grain structure modification takes place is generally called the heat-affected zone. The required interfacial heat can be supplied in a number of different ways, one of which is by capacitor discharge welding where a pulse of high current is passed across the weld part interface.

Figure 1:
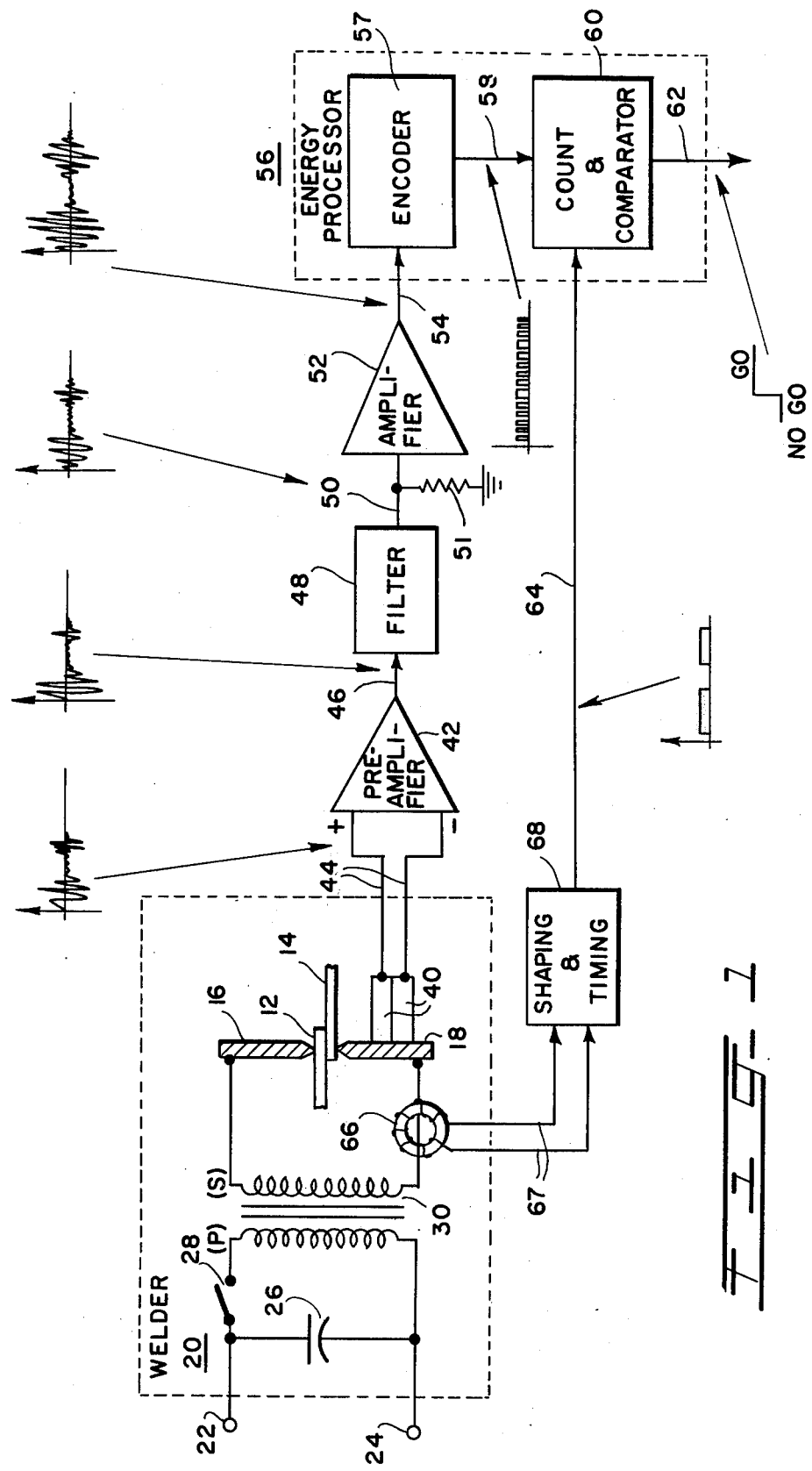
FIG. 1 is a simplified block diagram of a weld-evaluation system according to the present invention.

Referring now to FIG. 1, a pair of overlapping articles 12 and 14 comprising the same or different materials are positioned to be welded together between electrodes 16 and 18 of, for instance, a capacitance discharge welder 20. When a power source (not shown) is connected to terminals 22 and 24 of welder 20, capacitor 26 becomes charged. The closure of switch 28 discharges capacitor 26 through the primary winding (P) of transformer 30, causing a pulse of current to be delivered by the secondary winding (S) of transformer 30 to electrodes 16 and 18 and across the weld part interface. Capacitor 26 should be of sufficient size to deliver a pulse of current which will melt or plastically deform the weld area at the interface of articles 12 and 14.

Stress waves emitted from the weld area during both the weld pulse and post-weld intervals are detected by a piezoelectric differential transducer 40 (hereinafter referred to as sensor 40) of the present weld evaluation apparatus. Sensor 40 is shown as mechanically coupled to electrode 18 for non-contact detection purposes, but could also, for instance, be mechanically coupled to electrode 16 or either one of articles 12 and 14.

The signals which are detected by sensor 40 comprise waves which are: (a) generated by other electrical components in proximity to the system of FIG. 1, but not shown; (b) generated in articles 12 and 14, electrodes 16 and 18, or sensor 40 due to nontransient factors such as temperature and strain variations; and (c) stress waves, comprising bulk and surface waves, propagating from the weld nugget in articles 12 and 14, while the articles are being welded.

Whenever a phase transformation occurs in the weld nugget, energy is released in the form of stress waves, which waves, in turn, excite sensor 40. Depending on wave damping at the interfaces, the traveling mechanical stress impulses will cause sensor 40 to provide output voltage changes which are almost proportional to the amplitude of the impulses. Because of the low amplitude of the stress wave pulses, it is advantageous to provide for good transmission of the mechanical wave or amplification of the sensor's output voltage.

As shown in FIG. 1, sensor 40 is connected to a low-noise preamplifier 42 over leads 44. Preamplifier 42 should be of a design having a sensitivity which is preferably in the range of $1-4\mu V$, but can include a sensitivity beyond this range, as for example, $6\mu V$.

The output from preamplifier 42 is transmitted over lead 46 to a band-pass filter 48 which has a pass-band that falls at least partially within the natural frequency of sensor 40, but which falls without the range of noise frequencies generated by other components in proximity to the system. Filter 48 is preferably a fifth order, or higher, high-pass filter which is commercially available. A resistor 51 is preferably added to line 50 to match the input impedance of amplifier 52. The output of filter 48 on lead 50 is further amplified by amplifier 52. Amplifier 52 is of a design which advantageously has a fast slewing rate, such as, for example, a commercially available model 715 operational amplifier. The output of amplifier 52 is transmitted over lead 54 to an energy processor 56.

Energy processor 56 receives the amplified and filtered signal on lead 54 and measures the stress-wave energy released from the weld area during both the solid-to-liquid phase transformation and the post-weld liquid-to-solid phase transformation of the weld nugget.

Energy processor 56 can comprise circuitry which operates in accordance with a very fast analog-to-digital conversion scheme. Such circuitry, however, is very expensive.

Figure 3:
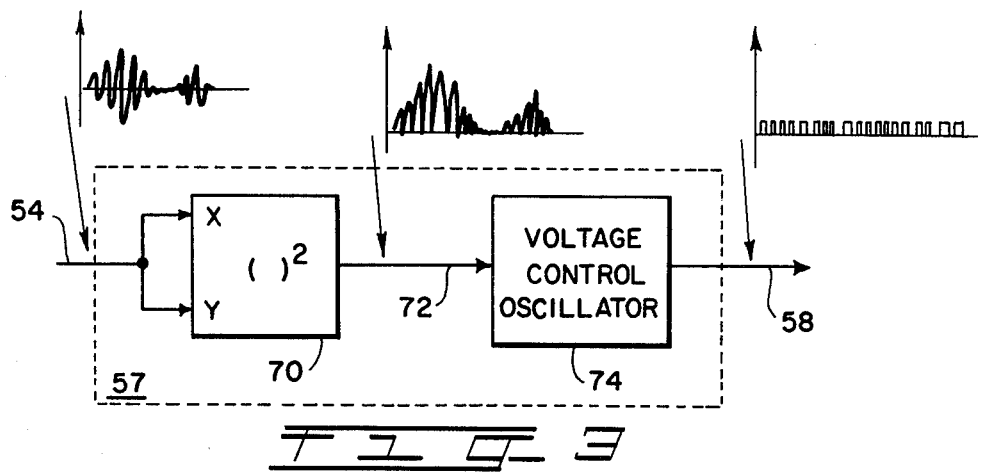
FIG. 3 is a simplified block diagram of an encoder for use with the energy processor of FIG. 1.
Figure 4:
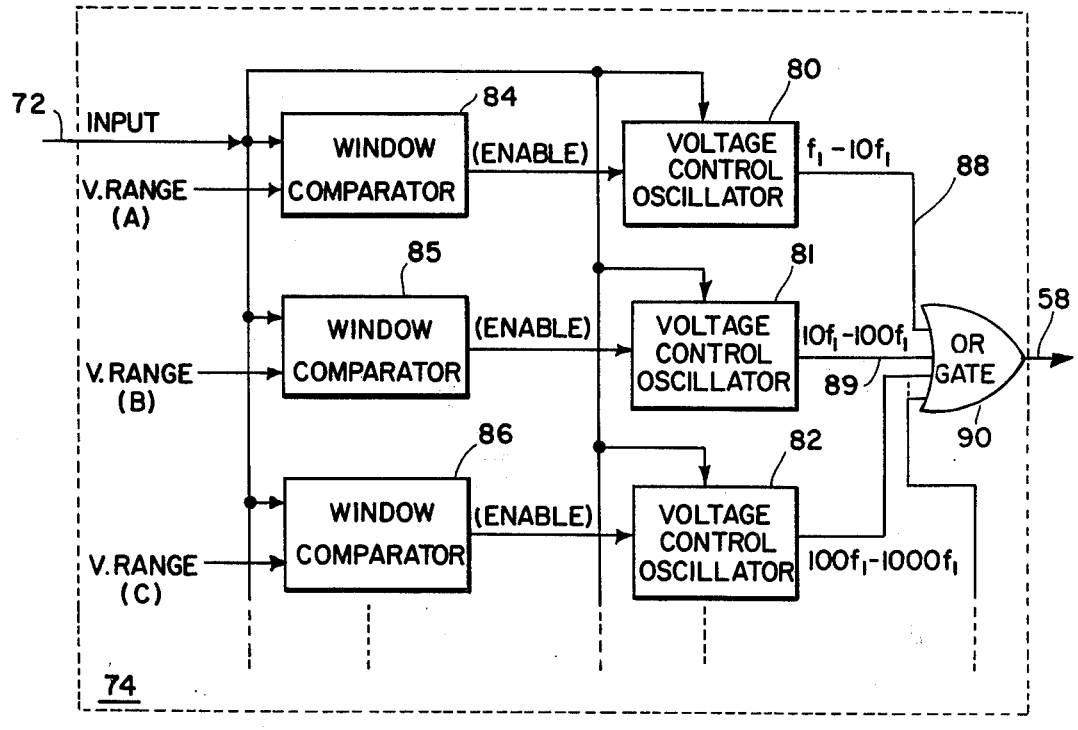
FIG. 4 is a simplified block diagram of a voltage control oscillator for use in the encoder of FIG. 3.

FIGS. 3 and 4 illustrate a novel energy processor 56 which provides very fast yet relatively inexpensive circuitry for use in the present weld evaluation system. Novel energy processor 56 includes an encoder 57 shown in FIG. 3 as comprising a multiplier circuit 70 which provides an output signal on lead 72 that is the square of the input signal of lead 54, and a voltage control oscillator 74. Multiplier 70 can comprise any known circuit such as, for example, a model 4456 multiplier from Teledyne-Philbric of Dedham, Mass. Voltage control oscillator 74 converts the squared amplitude modulated input signal on lead 72 into a digital frequency-modulated (FM) output signal, a change in the amplitude of the input signal causing a corresponding change in the rate, or frequency, of the digital pulses of the output signal.

Voltage control oscillator 74 should preferably comprise circuitry which provides a frequency range of approximately 1000:1. Since conventional voltage control oscillators generally provide a frequency range of up to 100:1, the novel voltage control oscillator circuitry 74 of FIG. 4 is preferably used in the present system. There, separate, commercially available voltage control oscillators (VCO) 80, 81, and 82 provide a digital FM output signal within the range of $f_1$ to $10f_1$, $10f_1$ to $100f_1$, and $100f_1$ to $1000f_1$, respectively. Each VCO 80, 81, and 82 has a separate respective window comparator 84, 85, and 86 associated therewith. Each window comparator 84, 85, and 86 compares the instantaneous voltage level of the input signal on lead 72 with a different portion of the overall input signal voltage range and provides an enable signal to the associated VCO 80–82 when the input voltage level falls within the associated voltage range under comparison. The input signal on lead 72 is also supplied to each of the VCOs 80–82.

In operation, if the input signal on lead 72 is assumed to include a voltage level which is rising through the entire ranges A and B, then window comparator 84 supplies an enable signal to VCO 80 for as long as the input voltage level is rising within range A. The enable signal from window comparator 84 causes VCO 80 to generate a digital FM output signal on lead 88 which increases from $f_1$ to $10f_1$ as the input voltage level correspondingly increases through range A. When the input voltage level reaches the lower edge of range B, window comparator 84 ceases to generate an enable signal to VCO 80 and window comparator 85 now supplies an enable signal VCO 81. The enable signal from window comparator 85 causes VCO 81 to generate a digital FM output signal on lead 89 which increases from $10f_1$ to $100f_1$ as the input voltage level correspondingly increases through range B. The output from each of VCOs 80–82 is coupled to a common OR gate 90 and onto lead 58 for transmission to a count and comparator circuit 60 of energy processor 56 (FIG. 1). It is, of course, possible to add further window comparators and VCOs in a manner shown in FIG. 4 to extend the range of operation. The voltage control oscillator circuitry 74 avoids the use of integrators which are generally limited in bandwidth and accuracy.

Figure 5:
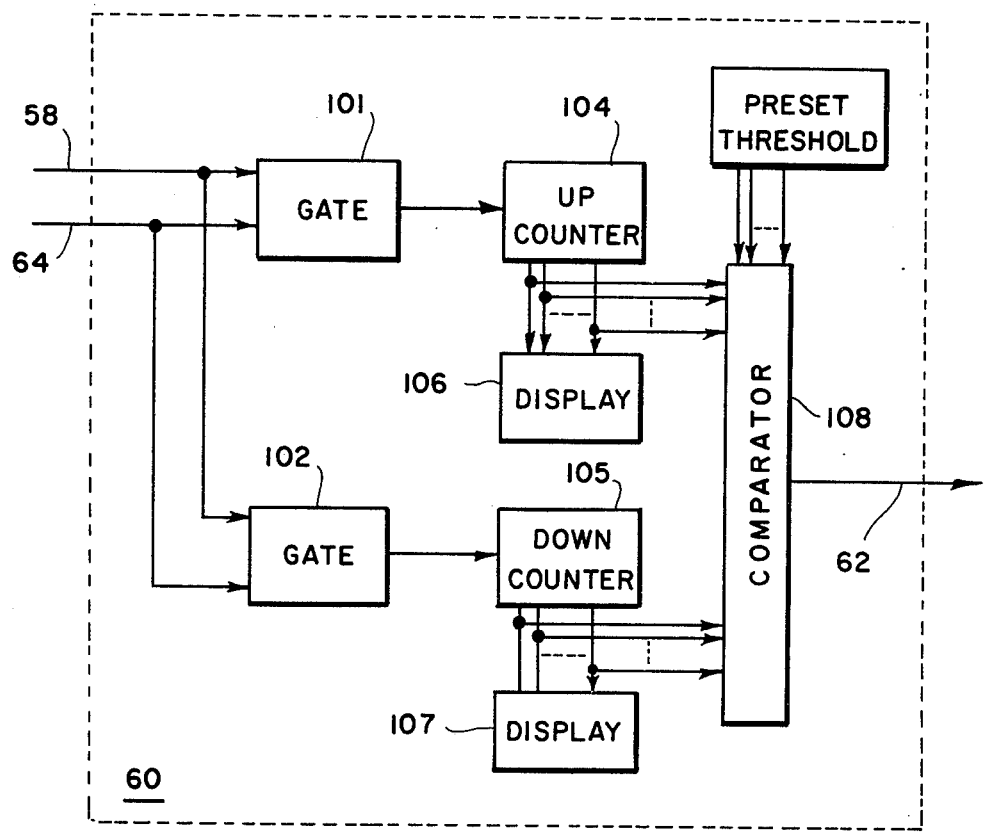
FIG. 5 is a simplified block diagram of a count and comparator circuit for use in the energy processor of FIG. 1.
Figure 6:
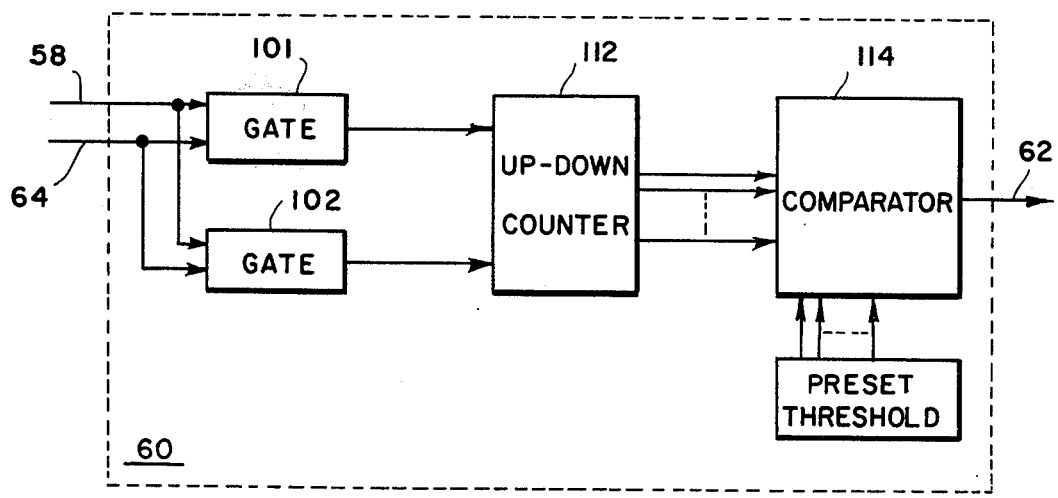
FIG. 6 is a simplified block diagram of another count and comparator circuit for use in the energy processor of FIG. 1.

The digital FM output signal from encoder 57 is transmitted over lead 58 to a count and comparator circuit 60 which forms another portion of energy processor 56. Count and comparator circuit 60 functions to separately count the input digital pulses relating to the solid-to-liquid phase transformation and the liquid-to-solid phase transformation of the weld, subtract the latter count from the former count, compare the net count value with a predetermined threshold value, and generate a go or no-go signal on lead 62 as a result of said comparison. FIGS. 5 and 6 illustrate two typical configurations which can be used in count and comparator circuit 60.

In FIGS. 5 and 6, the digital FM input signal on lead 58 is received at a first input of each of gates 101 and 102. Appropriate trigger pulses are received over leads 64 at a second input of each of gates 101 and 102. The appropriate trigger pulses first activate gate 101 for at least a portion of the weld period during which the solid-to-liquid phase transformation occurs in the weld area, and then activate gate 102 for at least a portion of the post-weld period during which the liquid-to-solid phase transformation occurs in the weld area. The activation of gate 101 permits the pulses on lead 58, representing the stress-wave energy detected during the solid-to-liquid phase transformation of the weld nugget, to be gated into counter 104. The activation of gate 102 permits the pulses on lead 58, representing the stress-wave energy detected during the liquid-to-solid phase transformation of the weld area, to be gated into counter 105. The combination of encoder 57 and counters 104 and 105 function in accordance with the equation:

$$E = \int_0^T v^2(t)dt$$

within a scale factor. The multiplier 70 squares the instantaneous waveform on lead 54, voltage control oscillator 74 provides a digital representation of the continuous integration of the squared waveform, and counters 104 and 105 provide a sum of the integration over the time period of the solid-to-liquid and liquid-to-solid phase transformations.

In FIG. 5 the energy counts stored in counters 104 and 105 are transmitted to display means 106 and 107, respectively, where the results can be visually observed or mechanically recorded for possible research purposes, and to a common comparator circuit 108. Comparator circuit 108 is adapted to subtract the count in counter 105 from the count in counter 104, to compare the net resultant value with a preset threshold value, and to generate a go or no-go signal on lead 62 dependent upon the results of the comparison.

An alternative arrangement for count and comparator circuit 60 is shown in FIG. 6. There, an up-down counter 112 replaces both the counters 104 and 105 and display means 106 and 107 of FIG. 5. In operation, when gate 101 is enabled, counter 112 counts the number of pulses transmitted on lead 58 in an increasing fashion. When gate 102 is next enabled, counter 112 then subtracts each pulse on lead 58 from the total count obtained during the period when gate 101 was activated. Comparator 114 compares the net value stored in counter 112, after gate 102 has been deactivated, with a preset threshold value to generate a go or no-go signal on lead 62 dependent on the results of the comparison. The go or no-go signal on lead 62 from count and comparator circuit 60 can be used to energize a visual or audible means (not shown) for indicating a good or bad weld.

It must, of course, be understood that (a) the greater the higher count in counter 104 differs from the count in counter 105, the greater the strength of the weld; and that (b) the preset threshold value corresponds to a minimal acceptable weld strength value, which value can be easily determined by, for example, destructively testing a number of sample welds formed using the present system, and correlating the determined strength with the measurements obtained in counters 104 and 105, or counter 112, for each of the sample welds.

It has been found that a relatively linear relationship exists between the net resultant stress wave energy value, as determined in comparator 108 of FIG. 5 and up-down counter 112 of FIG. 6, and the pull strength of a weld, regardless of the composition of each of articles 12 and 14. The relatively linear relationship exists independent of the weld energy supplied by welder 20 or the condition, such as cleanliness, of articles 12 and 14 at the interfacing surfaces being welded. Therefore, variations in weld energy or the condition of articles 12 and 14 will merely be reflected in variations in stress-wave energy along the linear curve, and in turn, in the strength of the weld.

The properly timed trigger pulses transmitted on leads 64 to gates 101 and 102 are preferably provided by a detecting means 66 positioned in welder 20 and a shaping circuit 68 connected between detecting means 66 (FIG. 1) and gates 101 and 102. Detecting means 66 is positioned in welder 20 to both detect the presence of a weld pulse as capacitor 26 discharges, and generate a signal in response thereto on leads 67 to shaping and timing circuit 68. Detecting means 66 can comprise any known form, such as, for example, a toroidal coil detector mounted in the secondary circuit of welder 22. Shaping and timing circuit 68 can comprise any known circuit which receives the signal from detecting means 66 and generates a trigger pulse to (a) gate 101 during the weld period where at least the solid-to-liquid phase transformation interval occurs in the weld area, and (b) gate 102 during the post-weld period where at least the liquid-to-solid phase transformation interval occurs in the weld area.

Figure 2:
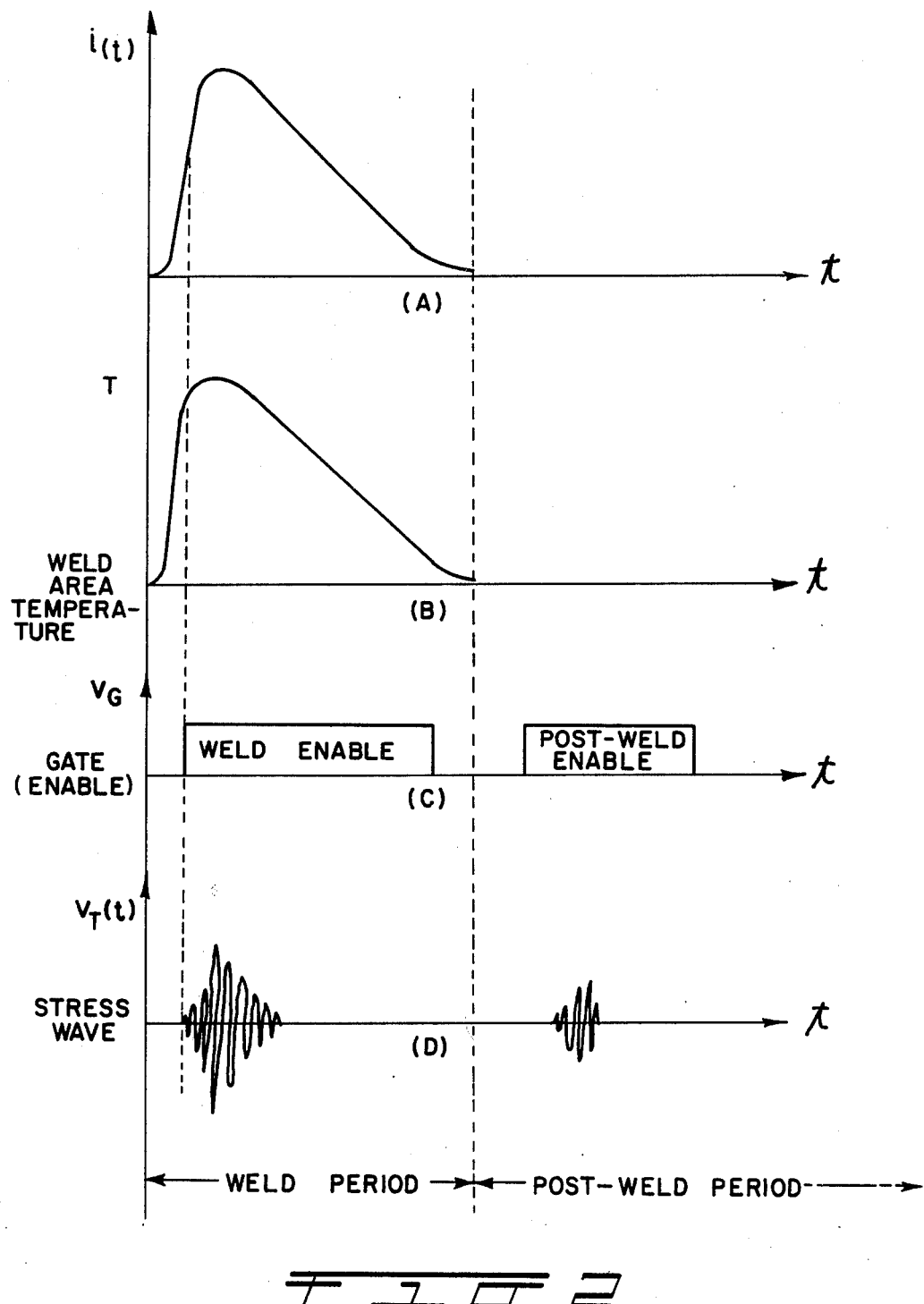
FIG. 2 illustrates various waveforms of the type which are displayed on an oscilloscope shown for purposes of explaining the present invention.

Referring particularly to FIG. 2, waveforms (A) to (D) typically illustrate various waveforms as they might normally appear on an oscilloscope connected to appropriate portions of the present weld evaluation system. Waveform (A) depicts the current pulse across the weld interface as delivered by secondary winding (S) of transformer 30 to electrodes 16 and 18 upon closure of switch 28 in welder 20. Waveform (B) depicts temperature variations occurring in the weld area in response to the current pulse of waveform (A) passing through the weld interface between articles 12 and 14. The temperature attains a peak during the period where melting or plastic deformation in the weld area occurs. Waveform (C) illustrates typical trigger pulses generated by shaping and timing circuit 68 which are transmitted to gating circuits 101 and 102 over leads 64. The weld enable pulse is used to enable gate 101 while th post-weld enable pulse is used to enable gate 102. Waveform (D) depicts stress waves detected by sensor 40 during the solid-to-liquid phase transformation interval (during weld period) and the liquid-to-solid phase transformation interval (during post-weld period). Typical waveforms found at various portions of the present system are also shown in FIGS. 1 and 3.

It is to be understood that the above-described embodiments are simply illustrative of the principles of the invention. Various other modifications and changes may be made by those skilled in the art which will embody the principles of the invention and fall within the spirit and scope thereof.

What is claimed is:

1. A voltage controlled oscillator circuit for receiving an analog input signal and generating an output frequency which is linearly proportional to the analog input signal, comprising:
   a plurality of window comparators for simultaneously receiving the analog input signal, each comparator being responsive to a predetermined different range of the maximum analog input signal amplitude to generate an enable signal; and
   a plurality of voltage control oscillators, for simultaneously receiving the analog input signal, each oscillator being responsive to the enable signal from a different one of the window comparators to generate a frequency-modulated output signal which is linearly proportional to the analog input signal within the predetermined range.

2. The voltage controlled oscillator circuit as set forth in claim 1 which further comprises:
   means for combining the frequency output signals to provide a continuous linear output from the voltage controlled oscillator circuit.

3. A signal processor for generating a digital frequency-modulated signal indicative of the energy of an analog input signal comprising a multiplier circuit for squaring the analog input signal and a voltage controlled oscillator circuit connected to said multiplier circuit for generating a digital frequency-modulated signal indicative of the energy of said squared signal from the multiplier circuit, wherein the voltage controlled oscillator further comprises:

a plurality of window comparators, each window comparator being adapted to both compare the squared signal from said multiplier circuit with a predetermined amplitude range representing a different portion of the maximum possible amplitude range for said squared signal, and generate an enable signal in response to the amplitude of said squared signal being within said respective predetermined amplitude range; and a pluraltiy of voltage controlled oscillators, each oscillator being associated with a separate one of said plurality of window comparators and adapted to generate a digital frequency-modulated signal, within a different predetermined frequency range, indicating the energy in said squared signal in response to said enable signal from the associated window comparator.

4. A signal processor for generating a digital frequency-modulated signal indicative of the energy (E) of an analog input signal over a period of time (T) in accordance with the equation:

$$E = \int_0^T v^2(t)dt,$$

where $(v)$ is the instantaneous signal voltage at time $(t)$; comprising a multiplier circuit for squaring said analog input signal, a voltage controlled oscillator circuit connected to the multiplier circuit for generating a digital frequency-modulated signal indicative of the energy of the squared signal from the multiplier circuit, and means for counting the pulses in said digital frequency-modulated signal during the period of time (T), wherein the voltage controlled oscillator further comprises:

a plurality of window comparators, each window comparator being adapted to both compare the squared signal from the multiplier circuit with a predetermined amplitude range representing a different portion of the maximum possible amplitude range for the squared signal and generate an enable signal in response to the amplitude of the squared signal being within said respective predetermined range; and a plurality of voltage controlled oscillators, each oscillator being associated with a separate one of said plurality of window comparators and adapted to generate a digital frequency-modulated signal, within a different predetermined frequency range, indicating the energy in said squared signal in response to said enable signal from the associated window comparator.

* * * * *

UNITED STATES PATENT OFFICE
CERTIFICATE OF CORRECTION

Patent No. 4,017,810    Dated April 12, 1977

Inventor(s) S. J. Vahaviolos

It is certified that error appears in the above-identified patent and that said Letters Patent are hereby corrected as shown below:

Column 3, line 43, "of lead 54" should read -- on lead 54 --;

line 57, "100:1" should read -- 10:1 --. Column 4, line 17, "signal VCO" should read -- signal to VCO --. Column 6, line 27, "th" should read -- the --.

*Signed and Sealed this*

Twenty-eighth *Day of* June 1977

[SEAL]

Attest:

RUTH C. MASON
*Attesting Officer*

C. MARSHALL DANN
*Commissioner of Patents and Trademarks*